United States Patent [19]

Savastano et al.

[11] Patent Number: 5,681,584

[45] Date of Patent: Oct. 28, 1997

[54] CONTROLLED RELEASE DRUG DELIVERY DEVICE

[75] Inventors: Louis Savastano, Livingston; James Carr, Butler, both of N.J.; Elizabeth Quadros, Brooklyn, N.Y.; Shailesh Shah, Union, N.J.; Satish Chaudra Khanna, Bottminger, Switzerland

[73] Assignee: Ciba-Geigy Corporation, Tarrytown, N.Y.

[21] Appl. No.: 622,238

[22] Filed: Mar. 22, 1996

Related U.S. Application Data

[63] Continuation of Ser. No. 165,437, Dec. 10, 1993, abandoned, which is a continuation-in-part of Ser. No. 52,435, Apr. 23, 1993, abandoned.

[51] Int. Cl.$^6$ ............................................. A61K 9/24
[52] U.S. Cl. ............................................. 424/473; 424/468
[58] Field of Search ............................................. 424/473, 468

[56] References Cited

U.S. PATENT DOCUMENTS

| | | | |
|---|---|---|---|
| 3,845,770 | 11/1974 | Theeuwes et al. | 128/260 |
| 4,627,851 | 12/1986 | Wong et al. | 604/892 |
| 4,693,895 | 9/1987 | Wong et al. | 424/473 |
| 4,705,515 | 11/1987 | Wong et al. | 604/892 |
| 4,857,336 | 8/1989 | Khanna et al. | 424/473 |
| 4,891,223 | 1/1990 | Ambegaonkar | 424/408 |
| 4,892,739 | 1/1990 | Shah et al. | 424/473 |
| 4,904,474 | 2/1990 | Theewes et al. | 424/424 |
| 5,001,161 | 3/1991 | Appelgren et al. | 514/651 |

FOREIGN PATENT DOCUMENTS

| | | |
|---|---|---|
| 0366621 | 5/1990 | European Pat. Off. |
| 0425699 | 5/1991 | European Pat. Off. |
| 425699 | 5/1991 | European Pat. Off. |
| 155898 | 9/1979 | United Kingdom |
| 8300435 | 2/1983 | WIPO |
| 9107949 | 6/1991 | WIPO |
| 9204011 | 3/1992 | WIPO |

OTHER PUBLICATIONS

Fara et al "Evaluation of Oxprenolol and Metoprolol Oros Systems in the dog" Br. J. Clin Phar. 19:91S–95S (1985).
Davis et al. "Gastrointestinal Transit of a Controlled Release Naproxen Tablet Formulation" J. Pharmaceuticals 32:85–90 (1986).
Davis et al "The Design & Evaluation of Controlled Release Systems for the Gastrointestinal Tract" Journal of Controlled Release 2:27–38 (1985).
Remington's Pharmaceutical Sciences 16th Ed. Mack, Easton, Pa. pp. 1594–1613 (1980).
Davis et al "Sticking of Dosage Forms in the GI Tract." 27(2):226, 1986 Feb.
Godbillon et al "Investigation of Drug Absorption From the Gastrointestinal Tract of Man." British Journal Clinical Phar. (1985) vol. 19, 1135–1185.
Davis et al "Transit of Pharmaceutical Dosage Forms Through the Smalll Intestine" Gut. 27:886–892. (1986).
Theeuwes "Elementary Osmotic Pump" Journal Pharmaceutical Sciences vol. 64, No. 12, (1975) 1987.–1991.
Rubinstein et al "Gastrointestinal Physiological Variables Affecting Performance of Oral Sustained Release Dosage Forms, Oral Sustained Release Formulations" Pergamon Press, Chap. 6. p. 146, Tables 9 and 10.
Brunton et al "Agents Affecting Gastrointestinal Water Flux and Motility" Goodman and Gilman's Pharmaceutical Basis of Therapeutics 8th Ed. Pergamon Press, Chap. 39, p. 915.
Dew et al "an Oral Preparation to Release Drugs in the Human Colon" Br. J. Clin. Pharmac. 14:405–408 (1982).
Davis et al "Biopharmaceutical Aspects of Solid Dosage Forms" Proceed. Intern. Symp Control. Rel. Bioact. Water. 15: 189–190 (1988).
Friend et al "Colon–Specific Drug Delivery" Advanced Drug Delivery Reviews 7:149–199 (1991).
Stevens et al "Pulsatile Drug Delivery to GI Tract" B.T. Gattefosse No. 84– 1991 (pp. 11–15).
Verhoeven et al "The Design of a Dry–Coated Controlled–Release Tablet for Oxprenolol with Microporus Polypropylene Powder" Journal of Controlled Release 10:205–217 (1989).
Kallstrand et al "Membrane–Coated Tablets: A System for the Controlled Release of Drugs" Journal of Pharmac. Sciences. vol. 72; No. 7; pp. 772–775 (1983).
Amkraut et al "Osmotic Delivery of Peptides and Macromolecules Advanced Drug Delivery Reviews", 4:255–276 (1990).
Barrow et al "Phathological Influences on Colonic Motility Implications for Drug Delivery" Advanced Drug Delivery Reviews 7:201–218 (1991).
Davis et al "A Comparative Study of the Gastrointestinal Transit of a Pellet and Tablet Formulation" International Journal of Pharmaceutics 21:167–177 (1984).

*Primary Examiner*—D. Gabrielle Phelan
*Attorney, Agent, or Firm*—Marla J. Mathias; Karen G. Kaiser; Irving M. Fishman

[57] ABSTRACT

A drug delivery device for delivering a drug either intermittently or to a pre-selected region of the gastro-intestinal tract, particularly to the colon, consists of an a solid core comprising an active agent coated with a delay jacket, then coated with a semi-permeable membrane which is optionally drilled to provide a release orifice, and then optionally further coated with an enteric material. The device delivers substantially all of the active agent to the targeted site.

23 Claims, No Drawings

5,681,584

CONTROLLED RELEASE DRUG DELIVERY DEVICE

This is a Continuation of Ser. No. 08/165,437, filed Dec. 10, 1993, now abandoned, which is a Continuation In Part of Ser. No. 08/052,435, filed on Apr. 23, 1993, now abandoned.

FIELD OF THE INVENTION

The present invention relates to tablets which are time-controlled to release active agent intermittently or at a pre-selected region of the gastro-intestinal tract, specifically the colon.

BACKGROUND OF THE INVENTION

Parametric drug delivery refers to drug release in synchrony with its temporal requirements or optimal absorption site, thereby maximizing therapeutic effect while simultaneously minimizing side-effects or in vivo degradation. An example of parametric drug delivery is delivery of a drag to a pre-selected region of the gastro-intestinal tract, such as the colon. Another example is delivery of a drug intermittently at pre-selected times such that the patient receives the drug when needed.

Delivery of a beneficial drug in the colon has been the goal of various research projects in the pharmaceutical industry. The reasons for this are multi-fold. To begin with, many drugs are rendered ineffective by the enzymes present in the fluids of the upper gastro-intestinal tract, particularly protein or peptide-like drugs. In addition, some drugs are more readily or more predictably absorbed by the colonic tissue than by that in the upper gastro-intestinal tract.

Delivery of a beneficial drug in the colon is also therapeutically indicated to treat diseased colonic tissue. In such circumstances, the drug should not be absorbed prior to localization in the colon lest its concentrations be diminished or even depleted prior to reaching the intended site of action. Such treatment would be beneficial for a variety of colonic diseases including inflammatory bowel disease, colitis ulcerosa, enteritis, regionalis Crohn, chronic nonspecific colitis, and diverticulitis.

Prior treatments have been attempted rectally using suppositories and enemas. Rectal administration, while often more effective than oral administration, is limited in that most rectally administrable dosage forms are capable of producing the intended result only in the immediate area, not reaching the upper portions of the colon. This is because the length of the colon reached is volume dependent, usually reaching only as far as the splenic flexure. In addition, rectal administration is messy and inconvenient, as well as not readily acceptable to the general patient population. Furthermore, if the patient suffers from severe inflammation of the rectum, he may experience difficulty with retention enemas.

Thus, an orally administrable dosage form to treat colonic diseases would usually be preferred and is often required. Orally administrable treatments, using tablets, capsules, and the like, have been attempted. However, to reach the colon intact, the dosage form must withstand the rigors of the transit through the gastro-intestinal tract. These rigors include at least a million-fold variation in hydrogen ion concentration, wide variations in osmotic pressure from the surrounding fluids, a variety of enzymes, and a strong mechanical grinding force.

Furthermore, most of these orally administered dosage forms result in delivery of the drug in the upper portion of the gastro-intestinal tract or, in the case of controlled release dosage forms, deliver drug throughout the entire length of the gastro-intestinal tract instead of concentrating delivery primarily within the colon. Thus, in either case, by the time the dosage form reaches the colon, the drug concentration is diminished or even depleted. In addition, the acidic and enzymatic environment of the stomach may inactivate a substantial mount of the drug, particularly protein or peptide-like drugs. Even if the drug is released from the stomach in its active state, such drugs frequently are metabolized or inactivated in the small intestine. Thus, little if any of the drug from these conventional dosage forms is available for producing a therapeutic result in the colon, especially if the dosage form reaches the colon essentially devoid of drug.

Drug delivery to the colon is difficult not only for the above mentioned facts, but also because of the uncertainty of the transit time from oral ingestion to arrival at this pre-selected site. The time of retention within the stomach is most variable, depending both on the size of the dosage form and the mount of food present at the time of ingestion. The drug delivery device may remain within the stomach from about 0.5 to about ten hours. The device then enters the small intestine where retention time is significantly more constant and less dependent upon the mount of food present. It takes from about three to about six hours to travel the length of the small intestine to the beginning of the colon. The device may then remain within the colon from about ten to about fourteen hours in a subject with normal motility.

Thus, the time span necessary to delay release of the drug from an orally administered dosage form until the beginning of the colon is wide. However, the time span can be considerably narrowed by measuring the time from arrival in the small intestine instead of from the time of ingestion. Drug delivery in the stomach may be prevented by the use of an enteric coating which is resistant to the gastric fluids. As such a coating is not soluble in fluids with an acidic pH, such as that of the stomach, application to the outside of the dosage form inhibits release prior to reaching the higher pH of the small intestine. Once the dosage form reaches the small intestine and the enteric coating dissolves, drug release needs to be delayed only an additional three to six hours to result in substantially no active agent being delivered before the colon.

Although some drug may reach the colon passively, conventional peroral dosage forms are not designed to deliver their contents specifically to the colon. Generally, they are formulated to be immediate release devices which disintegrate in the stomach, duodenum, or small intestine, allowing the drug to be immediately exposed to the local environment.

More recently, controlled release dosage forms, for example Orally Releasing Osmotic Systems or OROS® (Alza Corporation), have been developed (U.S. Pat. No. 3,845,770). Although the benefits of controlled release are significant, such as reduction in the number of doses and steady drug levels in the blood, they are generally no more effective than conventional tablets in delivering the active agent primarily to the colon.

Several delivery forms have been developed which attempt to deliver active agent primarily to the colon. These methods rely upon either the environmental conditions surrounding the system, particularly pH, bacterial count and/or time.

Wong, et at. (U.S. Pat. Nos. 4,627,851; 4,693,895; and 4,705,515) disclose a tri-laminated core in which the first layer is composed of an insoluble, but semi-permeable composition, the second is a microporous combination of water insoluble polymer and osmotic solute, and the third contains an enteric composition. This dosage form has a delayed onset of delivery for a period of about two hours after it exits the stomach, after which only about 50% of the drug is released within twenty-four hours. This drug delivery time scheme is insufficient to insure that the bulk of the drug is delivered to the colon.

Theeuwes, et al. (U.S. Pat. No. 4,904,474) disclose a dosage form which has a two-layered internal compartment with a first layer of the drug in an excipient layer adjacent to an exit passageway and a second layer of a push component. The internal compartment is surrounded by a semi-permeable wall and then an enteric layer. Theeuwes's dosage form results in a delay of the onset of delivery in intestinal fluid for a period of about two hours. This represents a delay period too short, and a delivery rate too slow to insure the bulk of the drug is delivered to the colon.

Ring, et at. (WO 91/07949) disclose a tablet core coated with two laminates. The outer laminate is an erodible acrylic polymer and the inner laminate consists primarily of amylose in the glassy state which can only be degraded in the presence of fecal microflorae.

The instant parametric drug delivery devices can also be used to deliver a drug intermittently at pre-selected times such that the patient receives the drug when needed. This is of particular importance in treating diseases which have symptoms which do not remain constant throughout the day and night.

For example, blood pressure is known to follow a circadian rhythm during a 24-hour period. In some subjects the highest pressure occurs in the morning shortly after the individual awakes, suggesting that it would be appropriate to deliver an antihypertensive agent such as a β-blocker to such a patient sufficiently before awakening so as to mitigate the effects of the disease at the most appropriate time interval. In order to accomplish this without disturbing the patient's sleep, it is necessary to administer the drug in the evening in a form that is activated just before the patient arises.

Another example is the treatment of asthma with the agent theophylline. The drug has a rather narrow therapeutic index with minimum effective blood concentrations of 6–10 µg/ml and toxic levels of approximately 20 µg/ml. However, the serum theophylline concentrations required to produce maximum physiological benefit may fluctuate with the degree of bronchospasm present and are variable. Asthma often exhibits more serious symptoms in the evening, while theophylline absorption may change due to posture and changes in the circadian rhythm. This suggests that the nighttime dosing need not be identical to the daytime dosing regimen, and it is recommended that the extended release formulation not be given in the evening. Thus, a sustained acting dosage form for the day, with a bolus dose of theophylline at bedtime combined into a single peroral drug delivery system requiring once per day dosing in the evening is of possible benefit.

Many controlled release dosage forms are created by the use of special water insoluble membranes which either limit the flow of gastro-intestinal juices into the system, or modulate the release of dissolved substances out of the system. Application of such a membrane was initially accomplished by thin layer, spray application of lacquer coatings made with organic solvents. These processes allowed the manufacturer to achieve the desired membrane qualities in short time using few components. However, it was eventually realized that the processes were often dangerous in that excessive use of organic solvents were capable of causing irreversible harm to the environment and produced dosage forms which contained extraneous, undesirable residuals.

Whenever organic solvent is used in a pharmaceutical process, measures need to be taken to protect the operators who produce the dosage forms and the environment from overexposure to the hazardous, often teratogenic and carcinogenic materials. Additional precautions are necessary to protect personnel, equipment and facilities from harm due to the ignition of explosive vapors. Even if these immediate problems can be solved through engineering means, it is still possible for detectable levels of residual solvent to remain in the finished dosage form, the long term effects of which are either undesirable or not yet established.

Several manufacturers of coating equipment responded to the challenge of minimizing the dangers of using hazardous solvents by building machines which contained and controlled the exhaust vapors from organic solvent coating processes. Despite the capability of these machines to minimize the problems of explosion and exposure hazards, the equipment is complicated, costly to operate, and requires rather expensive maintenance even on a murine basis. It also does not address the problem of residual solvent remaining in the finished dosage form. This is ameliorated by storing the coated tablets in containers at high temperatures and humidities in order to draw the solvent out of the tablets; however, solvent extraction from finished dosage forms adds costs to the manufacturing process in additional capital equipment expenditures, processing time and analytical requirements.

The impetus for seeking new manufacturing techniques is obvious. The U.S. Food and Drug Administration and Environmental Protection Agency are continuously urging all manufacturers to reduce, and wherever possible, to eliminate the use of organic solvents in manufacturing.

Rather than pursuing costly engineering solutions to the problem, raw material suppliers were encouraged to develop aqueous dispersions of the materials most frequently employed to produce film coatings for tablets, pellets and particulate dosage forms. Aqueous dispersions allow utilization of existing equipment and familiar processes, thus avoiding the expenses of capital investments, maintenance, process validation and retraining of personnel.

SUMMARY OF THE INVENTION

It is accordingly an object of the present invention to provide a delivery device for the oral administration of a pharmaceutically acceptable active agent to a warm-blooded animal, either intermittently at pre-selected times or to a pre-selected region of the gastro-intestinal tract, particularly to the lower portion of the small intestine and/or the colon, more particularly to the colon.

It is another object of this invention to provide a dosage form for delivering substantially all of a therapeutic drug to the colon.

It is yet another object of this invention to provide a dosage form which comprises a core tablet coated with a delay jacket for delaying the delivery of the drug to insure the time required for the dosage form to travel through the small intestine.

It is still yet another object of this invention to provide a dosage form in which the semi-permeable membrane may be applied without the use of organic solvents, ie. aqueously, yet is still strong enough to resist the hydrostatic pressures of the ordinary osmotic core.

It is a further object of this invention to provide a dosage form which comprises an enteric coating over a semi-permeable wall for further delaying the delivery of the active agent during the time required for the dosage form to travel through the stomach.

It is still a further object of this invention to provide a dosage form which resists dissolution in gastric fluid for at least two hours, further delays initiation of active agent release for at least three hours, and releases at least 70% of its active agent within twenty-four hours.

It is yet still a further object of this invention to provide a delivery device which delivers drag intermittently at pre-selected times.

These, and other objects apparent to those skilled in the art from the following detailed description, am accomplished by the present invention which pertains to the delivery of a therapeutic drug to a pre-selected region of the gastro-intestinal tract, particularly the colon, by means of a drug delivery device. This drug delivery device comprises:

a) a solid core comprising an active agent;
b) a delay jacket coated over the core;
c) a semi-permeable membrane coated over the delay jacket, the membrane optionally having a release orifice; and optionally
d) an enteric coating over the semi-permeable membrane.

DETAILED DESCRIPTION OF THE INVENTION

This invention pertains to an osmotic delivery device for the oral administration of a pharmaceutically acceptable active agent to a warm-blooded animal, either intermittently at pre-selected times or to a pre-selected region of the gastro-intestinal tract, particularly to the lower portion of the small intestine and/or the colon, more particularly to the colon. This drug delivery device comprises:

a) a solid core comprising an active agent;
b) a delay jacket coated over the core;
c) a semi-permeable membrane coated over the delay jacket, the membrane optionally having a release orifice; and optionally
d) an enteric coating over the semi-permeable membrane.

Such device with an enteric coating thus resists dissolution in gastric fluid for at least two hours and thereafter limits the release of active agent in intestinal fluid to approximately ten percent or less for at least three hours after the device passes through the pylorus due to the delay jacket. The device thus allows for controlled continuous release of the active agent in the pre-selected region of the gastro-intestinal tract at a predetermined average rate, preferably at a rate of about 5 percent to about 25 percent by weight per hour. In addition, the device allows for substantially all of the active agent to be released at the pre-selected region of the gastro-intestinal tract, preferably 70–100% within twenty-four hours of ingestion.

Preferably, the basic device releases its active agent in vitro according to the following scheme, where time is hours from inception corresponding to in vivo release of active agent from time of ingestion:

| Time (hrs.) | Fluid | Total Amount Released (%) |
| --- | --- | --- |
| 2 | gastric | 0–4 |
| 5 | intestinal | 0–10 |

-continued

| Time (hrs.) | Fluid | Total Amount Released (%) |
| --- | --- | --- |
| 6 | intestinal | 0–20 |
| 8 | intestinal | 0–50 |
| 10 | intestinal | 10–80 |
| 12 | intestinal | 20–100 |
| 18 | intestinal | 50–109 |
| 24 | intestinal | 70–115 |

Thus, the colonic delivery device would deliver from about 50% to about 100%, more particularly from about 60% to about 90%, most particularly from about 70% to about 80% of its active agent to the colon.

The solid core comprises an active agent and may optionally include other pharmaceutically acceptable excipients including osmotic agents, lubricants, glidants, wetting agents, binders, fillers, and suspending/thickening agents. Any core which would be suitable for an OROS-type system may be used in the present invention, including the various modifications currently known in the art such as MOCOS™ and push-pull OROS.

As used herein, MOCOS refers to a mono-compartmental system, such as that described in U.S. Pat. No. 4,857,336, hereby incorporated by reference, in which the elementary OROS has been modified in that the core comprises a hydrogel in addition to an active agent and an osmotic agent; and push-pull OROS refers to a system, such as that described in U.S. Pat. No. 4,111,202 (equivalent to Great Britain Patent 1,551,898), hereby incorporated by reference, in which the core has a drug layer immediately adjacent to the release orifice, a "push" layer consisting of hydrogels and osmotic agents beneath the drug layer, and an optional partition layer between the two.

Active agents useful in the present invention include, but are not limited to, proteins and peptides, antiasthmatics, antianginals, corticosteroids, 5-lipoxygenase inhibitors, antihypertensives, and leukotriene $B_4$ receptor antagonists. Proteins and peptides include, but are not limited to, transforming growth factors (TGF), immunoglobulin E (IgE) binding factors, interleukins, interferons (IFN), insulin-like growth factors (IGF), milk growth factors, anticoagulants, and parathyroid hormones (PTH). Specific active agents include, but are not limited to theophylline, IGF-I, PTH (1–34) and analogues thereof, $TGF_\alpha$,$TGF_{\beta 1}$, $TGF_{\beta 2}$,$TGF_{\beta 3}$, $IFN_\alpha$, hybrid $IFN_\alpha$, $IFN_\gamma$, hirudin, heparin, calcitonin, 5-aminosalicylic acid, CGS 23885, CGS 25019C, CGS 26529, Zileuton, ONO-LB 457, beclomethasone dipropionate, betamethasone-17-valerate, prednisolone metasulfobenzoate, tixocortol pivalate, budesonide, fluticasone, metoprolol fumarate, metoprolol tartrate, tetrahydroaminoacridine (THA), galanthamine, ursodiol, clomipramine hydrochloride, terbutaline sulfate, aminoglutethimide, deferoxamine mesylate, estradiol, isoniazid, methyltestosterone, metyrapone, and rifampin. Of particular importance are theophylline, IGF-I, PTH (1–34) and analogues thereof, $TGF_\alpha$,$TGF_{\beta 1}$, $TGF_{\beta 2}$,$TGF_{\beta 3}$,$IFN_\alpha$, hybrid $IFN_\alpha$, $IFN_\gamma$, hirudin, heparin, calcitonin, 5-aminosalicylic acid, CGS 23885, CGS 25019C, CGS 26529, Zileuton, ONO-LB 457, beclomethasone dipropionate, betamethasone-17-valerate, prednisolone metasulfobenzoate, tixocortol pivalate, budesonide, fluticasone, and metoprolol. Virtually any other active agent which is known to be colonically absorbable or used to topically treat the colon can be used as an active agent in the present invention as long as it is compatible with the system components.

As used herein, the active agents CGS 23885, 25019C, CGS 26529, Zileuton, ONO-LB 457 are defined as follows:

CGS 23885 refers to N-hydroxy-N-((6-phenoxy-2H-1-benzopyran-3-yl)methyl)-urea; CGS 25019C refers to 4-[5-[4-(aminoiminomethyl)phenoxy]pentoxy]-3-methoxy-N,N-bis(1-methylethyl)benzamide (Z)-2-butenedioate; CGS 26529 refers to N-[2-[[2-[[4-(4-fluorophenyl)phenyl]methyl]-1,2,3,4-tetrahydro-1-oxo-6-isoquinolinyl]oxo]ethyl]-N-hydroxyurea; Zileuton refers to 1-(1-benzo[b]thien-2-ylethyl)-1-hydroxyurea; ONO-LB 457 refers to 5-[2-(2-carboxyethyl)-3-{6-(para-methoxyphenyl)-5E-hexenyl}oxyphenoxy] valeric acid.

The core may include an osmotic agent if necessary or desirable to effect the desired release profile. The active agent, for example, metoprolol fumarate, may be sufficiently soluble to induce an internal hydrostatic pressure acceptable to eliminate the need for any additional osmotic agent. Typically, however, an additional compound will be included as the osmotic agent so as to promote the dissolution and release of the core active agent. The osmotic agent is a water-soluble compound which induces a hydrostatic pressure after water penetrates the semi-permeable membrane to drive out the active agent as a solution or a suspension. Suitable osmotic agents include any number of agents having a suitably high solubility and dissolution rate. The osmotic agent may be selected from any pharmaceutically acceptable chemical entity which is inert to the system. Suitable osmotic agents include pharmaceutically acceptable salts of inorganic and organic acids or nonionic organic acids of particularly high water solubility, e.g. carbohydrates such as sugar, or amino acids, or another active agent possessing suitable solubility.

Examples of such water-soluble compounds for inducing osmosis in the core include inorganic salts such as sodium, potassium or magnesium chloride, or sodium or potassium hydrogen or dihydrogen phosphate; salts of organic acids such as sodium alginate, sodium ascorbate, sodium benzoate, sodium citrate, edetate disodium, sodium fumarate, sodium or potassium acetate, or magnesium succinate; organic acids such as alginic acid, ascorbic acid, citric acid, edetic acid, malic acid, or sorbic acid; carbohydrates such as dextrates, sorbitol, xylitol, maltitol, mannitol, arabinose, ribose, xylose, glucose, dextrose, fructose, galactose, mannose, sucrose, maltose, lactose, or raffinose; water-soluble amino acids such as glycine, leucine, alanine or methionine; or miscellaneous others such as magnesium sulfate, magnesium carbonate, urea, saccharin, sodium saccharin, glycerin, hexylene glycol, polyethylene glycol, or propylene glycol; and mixtures thereof.

Additional core excipients may include tabletting lubricants, glidants, wetting agents to aid in dissolution of the components, binders, and suspending/thickening agents. Suitable lubricants include, but are not limited to, calcium stearate, glyceryl behenate, hydrogenated vegetable oils, magnesium stearate, mineral oil, polyethylene glycol, sodium stearyl fumarate, stearic acid, talc, and zinc stearate. Suitable glidants include, but are not limited to, fused or colloidal silicon dioxide, calcium silicate, magnesium silicate, talc, and silica hydrogel. Suitable wetting agents include, but are not limited to, benzalkonium chloride, benzethonium chloride, cetylpyridinium chloride, docusate sodium, lecithin, nonoxynol 9, nonoxynol 10, octoxynol 9, poloxamer, polyoxyl 35 castor oil, polyoxyl 40 hydrogenated castor oil, polyoxyl 50 stearate, polyoxyl 10 oleyl ether, polyoxyl 20 cetostearyl ether, polyoxyl 40 stearate, polysorbate 20, polysorbate 40, polysorbate 60, polysorbate 80, sodium lauryl surfate, sorbitan esters, polyoxyethylene sorbitan fatty acid esters, and Tyloxapol (4-(1,1,3,3-tetramethylbutyl)phenol polymer with formaldehyde and oxirane). Suitable binders include, but are not limited to, acacia, alginic acid, carboxymethylcellulose sodium, dextrin, ethylcellulose, gelatin, glucose, guar gum, hydroxyethyl cellulose, hydroxypropyl methylcellulose, hydroxypropyl magnesium aluminum silicate, methylcellulose, microcrystalline cellulose, polyethylene oxide, polymethylmethacylates, polyvinylpyrrolidone, pregelatinized starch, sodium alginate, syrup, and zein. Suitable suspending/thickening agents include acacia, agar, alginic acid, bentonite, carbomer, carboxymethylcellulose calcium, carageenan, carboxymethylcellulose sodium, corn starch, dextrin, gelatin, guar gum, hydroxyethyl cellulose, hydroxypropyl cellulose, hydroxypropyl methylcellulose, kaolin, lecithin, magnesium aluminum silicate, methylcellulose, microcrystalline cellulose, pectin, poloxamer, polyethylene glycol alginate, polyethylene oxide, polyvinyl alcohol, polyvinylpyrrolidone, vinyl acetate, powdered cellulose, pregelatinized starch, propylene glycol alginate, silicon dioxide, sodium alginate, tragacanth, and xanthan gum.

The delay jacket is included to impede the dissolution and release of the active agent for the time necessary for the drug delivery device to travel through the small intestine. It comprises soluble materials, but may contain insoluble materials as well. The delay jacket must be capable of attracting water across the semi-permeable membrane while at the same time hindering the water from reaching the active core for the designated period of delay. Thus, the delay jacket will typically contain both water soluble, osmotically active components and insoluble and/or swellable components. The soluble osmotic agents leach out of the jacket and a suspension of at least some of the insoluble and/or swellable components remains. The active agent will later diffuse through this remaining suspension and thus the release of the active agent is dependent not only upon the composition of the inner core, but also upon the composition of the jacket.

The delay jacket typically comprises a binder, an osmotic agent, and a tablet lubricant. Suitable binders include, but are not limited to, acacia, alginic acid, carboxymethylcellulose sodium, dextrin, ethylcellulose, gelatin, glucose, guar gum, hydroxyethyl cellulose, hydroxypropyl methylcellulose, hydroxypropyl magnesium aluminum silicate, methylcellulose, microcrystalline cellulose, polyethylene oxide, polymethylmethacrylates, polyvinylpyrrolidone, pregelatinized starch, sodium alginate, syrup, and zein. Suitable osmotic agents include, but are not limited to, inorganic salts such as sodium, potassium or magnesium chloride, or sodium or potassium hydrogen or dihydrogen phosphate; salts of organic acids such as sodium alginate, sodium ascorbate, sodium benzoate, sodium citrate, edetate disodium, sodium fumarate, sodium or potassium acetate, or magnesium succinate; organic acids such as alginic acid, ascorbic acid, citric acid, edetic acid, malic acid, or sorbic acid; carbohydrates such as dextrates, sorbitol, xylitol, maltitol, mannitol, arabinose, ribose, xylose, glucose, dextrose, fructose, galactose, mannose, sucrose, maltose, lactose, or raffinose; water-soluble amino acids such as glycine, leucine, alanine or methionine; or miscellaneous others such as magnesium sulfate, magnesium carbonate, urea, saccharin, sodium saccharin, glycerin, hexylene glycol, polyethylene glycol, or propylene glycol; and mixtures thereof. Suitable tablet lubricants include, but are not limited to, calcium stearate, glyceryl behenate, hydrogenated vegetable oils, magnesium stearate, mineral oil, polyethylene glycol, sodium stearyl fumarate, stearic acid, talc, and zinc stearate.

Additional jacket excipients may include glidants and wetting agents. Suitable glidants include, but are not limited to, fused or colloidal silicon dioxide, calcium silicate, magnesium silicate, talc, and silica hydrogel. Suitable wetting agents include, but are not limited to, benzalkonium chloride, benzethonium chloride, cetylpyridinium chloride, docusate sodium, lecithin, nonoxynol 9, nonoxynol 10, octoxynol 9, poloxamer, polyoxyl 35 castor oil, polyoxyl 40 hydrogenated castor oil, polyoxyl 50 stearate, polyoxyl 10 oleyl ether, polyoxyl 20 cetostearyl ether, polyoxyl 40 stearate, polysorbate 20, polysorbate 40, polysorbate 60, 80, sodium lauryl sulfate, sorbitan esters, polyoxyethylene sorbitan fatty acid esters, and Tyloxapol (4-(1,1,3,3-tetramethylbutyl)phenol polymer with formaldehyde and oxirane).

Certain excipients may be included within the device to serve more than one function. For example, glucose may be included as a binder and/or an osmotic agent, and talc may be included as a glidant and/or a lubricant.

The composition of the delay jacket should be tailored to the composition, type of core, and type of membrane used. For example, if a MOCOS-type core is used, additional suspending or thickening agent in the delay jacket would be unnecessary. The MOCOS core already contains sufficient excipients to induce expression of the active agent through the release orifice or the membrane pores in the form of a suspension. If additional suspending or thickening agents were to be used to form the delay jacket, the active agent would probably be caught in the suspension and thus not be released from the delivery device. A completely soluble jacket would therefore be preferred in the case of a MOCOS-type core, for example, a soluble jacket composed of dextrates, hydroxypropyl methylcellulose, polyethylene glycol, and magnesium stearate.

The delay jacket may be applied to the core using conventional means known in the technology, for example by using a tablet press or a spray coater. If applied as a solid, the delay jacket is preferably between about 125% and about 275%, and more preferably between about 150% and about 250% of the core by weight. If applied as a liquid, the delay jacket is preferably between about 10% and about 100%, more preferably between about 20% and about 80%, and most preferably between about 30% and about 60% of the core by weight. However, in both cases the ranges will vary considerably based on the solution/suspension properties of the materials selected, and on the permeability properties of the rate controlling membrane.

The semi-permeable membrane is intended to be rigid enough so as to maintain the physical integrity of the tablet of the invention even in its environment of use without adversely affecting the active agent. The term "semi-permeable," as defined herein, refers to a membrane which, under identical conditions, transports different molecular species at different rates. In this case, the membrane is permeable to gastro-intestinal fluids, yet may or may not be permeable to the active agent or osmotic agent. If it is impermeable to the solubilized or suspended active agent or osmotic agent, it is necessary to include at least one release orifice through the membrane, while if it is permeable to the active agent or osmotic agent, the release orifice is optional.

The membrane comprises a material which can form films and typically comprises any of the porous membrane materials known in the tabletting art. Typical materials for forming the membranes are those known in the art to form osmosis or reverse osmosis membranes, including polycation-polyanion membranes. The porous membrane materials include, but are not limited to, cellulose acetate, ethylcellulose, polymethacrylic acid esters and acrylic acid ester/methacrylic acid copolymer with quarternary ammonium groups, cellulose triacetate, agar acetate, amylose triacetate, beta glucan acetate, beta glucan triacetate, cellulose acetate ethyl carbamate, cellulose acetate phthalate, cellulose acetate methyl carbamate, cellulose acetate succinate, cellulose acetate dimethylaminoacetate, cellulose acetate ethyl carbonate, cellulose acetate methyl sulfonate, cellulose acetate butyl sulfonate, cellulose ethers, cellulose acetate propionate, polyvinyl methyl ether polymers, cellulose acetate laurate, methyl cellulose, cellulose acetate p-toluene sulfonate, triacetate of locust bean gum, cellulose acetate with acetylated hydroxyethyl cellulose, hydroxylated ethylenevinylacetate, polymeric epoxides, alkylene oxide-alkyl glycidyl ethers, polyurethanes, and polyglycolic acid. Preferably, the membrane material is cellulose acetate, ethylcellulose, polymethacrylic acid esters and acrylic acid ester/methacrylic acid copolymer with quarternary ammonium groups.

Alternatively, the semi-permeable membrane may be comprised of non-porous membrane materials in which pores have been formed. Typically, this is accomplished by including a water soluble pore-forming material in the insoluble, non-porous membrane material solution. When the membrane is exposed to an aqueous environment, the pore-forming material dissolves, resulting in the formation of pores. Thus, the porosity of the membrane is directly proportional to the amount of pore-forming material incorporated into the membrane. The non-porous membrane materials include, but are not limited to, acrylics, polyurethanes, silicones, polyethylenes, polyvinyl chlorides, and ethylcellulose. The pore-forming materials include, but are not limited to, lactose, sucrose, mannitol, polyethylene glycol (PEG), hydroxypropylmethylcellulose (HPMC) and surfactants or other soluble additives.

The semi-permeable membrane may be applied using conventional film coating techniques known in the art, for example fluidized bed spraying. The choice of semi-permeable membrane plays an important role in controlling the release of the active agent. For example, it is known that the acetyl value is an important factor in determining the release rate from membranes constructed from cellulose acetate. Compendial grade cellulose acetate is commercially available with nominal acetyl values of either 32% or 40%. Membranes constructed from material at 32% acetyl value release drug from similar drug cores at a faster rate than do membranes constructed with the same amount of cellulose acetate by weight having a 40% acetyl value.

Further, the membrane may be applied without the use of organic solvents, for example as an aqueous dispersion. Although most of the above-mentioned membrane materials may be applied aqueously, the preferred membrane materials in this case include methacrylic ester copolymers, poly (ethyl acrylate, methyl methacrylate) [for example, EUDRAGIT® NE 30 D], poly(ethyl acrylate, methyl methacrylate, trimethylammonioethyl methacrylate chloride) [for example, EUDRAGIT® RL or EUDRAGIT® RS], polymethyl methacrylate-methacrylic acid copolymers, cellulose acetate, and ethylcellulose, and combinations thereof.

The major problem in utilizing aqueous dispersions to provide a controlled release membrane is that these membranes do not generally have the same tenacity as membranes which am applied using organic solutions. This lack of tenacity often results in the membrane rupturing from the build-up of hydrostatic pressure within the delivery device, dumping the contents rather than releasing the drug at a controlled rate.

Therefore, when the colonic delivery device is prepared with an aqueously applicable membrane, it is important that the delay jacket components do not include significant amounts of insoluble, swellable materials which cannot be expressed through either the release orifice or the membrane. This limitation aids in preventing excessive hydrostatic pressure from forming within the device and rupturing the membrane, thus allowing controlled drug release to occur. For example, insoluble polysaccharides like starch and cellulose which have high water swelling capabilities should be avoided, but soluble hydrogels, such as polyethylene glycol, hydroxypropyl methylcellulose and hydroxyethyl cellulose, can be included.

One or more release orifices may be included through the semi-permeable membrane. This release orifice is included to allow passage of the active agent and the soluble excipients, either in addition to or as an alternative to the pores of the semi-permeable membrane. It can be used to further control the release rate of the active agent by varying its size. Typically, the size of the release orifice is between about 0.05 mm and about 1.5 mm, more narrowly between about 0.15 mm and about 0.40 mm for elementary OROS, however, this range is considerably higher for more complicated systems such as MOCOS which utilize viscous hydrogel polymers. The release orifice may be added using conventional techniques known in the art, for example by drilling, either mechanically or by use of a laser. Further, at least one preferential weak spot may be created within the coating such that the pressure which builds up within the device causes a breakthrough in the coating at such weakened areas.

The enteric coating is included to prevent the dissolution of the jacket and core in the stomach. It may consist of any pharmaceutically acceptable material which is gastric fluid resistant, that is a material soluble only in fluids with a pH greater than that of the stomach. Enteric coating materials include, but are not limited to, cellulose acetate phthalate NF, hydroxypropyl methylcellulose phthalate NF, polyvinyl acetate phthalate NF, and methacrylic acid copolymer NF. Thus, in a low pH environment, the enteric coating will be insoluble and hinder intrusion of water through the semi-permeable membrane which could otherwise dissolve the delay jacket. It may be applied over the semi-permeable membrane using conventional film coating techniques known in the art, for example perforated pan coating.

Upon ingestion, the drug delivery device encounters the acidic gastric fluid, but remains intact because of the enteric coating. After the stomach pushes the device through the pylorus into the duodenum, the device is exposed to fluids of higher pH and the enteric coating dissolves. Once the semi-permeable membrane is exposed to these fluids, the device is activated. Water from the gastro-intestinal tract is imbibed through the membrane by diffusion and begins to selectively dissolve the delay jacket. As the soluble components of this delay jacket are selectively dissolved, they are released either through the membrane, or through the release orifice, until they are depleted. The delay jacket directly under the membrane prevents water from reaching the active drug core, thus providing the delayed release of the active agent. Once the delay jacket has been exhausted of soluble components, a suspension of insoluble material held in place by the membrane, continues to surround the active drug core. Eventually, the active core is reached by the water, increasing the pressure within the membrane as the core osmotic agents imbibe more and more water. As the drug is dissolved or suspended, this hydrostatic pressure forces the active agent through the membrane and/or through the release orifice to deliver the drug at a controlled rate. The release rate of the drug is based on the osmotic properties of the core, the solubility of the drug and excipients, and the water permeation rate through the membrane, and to a more limited extent, the viscosity of the solution or suspension, the suspension of material from the depleted delay jacket, and the size of the membrane pores or release orifice.

As an extension to the basic device, a further layer of active agent may be included to deliver an initial burst of active agent prior to the device reaching the colon. This active agent may be the same as or different from that within the core. The additional active agent layer may be applied over the enteric coating to deliver an immediate release of active agent. Alternatively, this additional layer may be applied under the enteric layer for release in the upper portion of the small intestine.

To deliver active agent intermittently, the basic device is altered by including an additional layer of active agent between the delay jacket and the membrane. This active agent layer comprises an active agent and may optionally include other pharmaceutically acceptable excipients including osmotic agents, lubricants, glidants, wetting agents, binders, fillers, and suspending/thickening agents.

In this alternative device, water from the gastro-intestinal tract is imbibed through the membrane by osmosis and dissolves or suspends the active agent layer. The active agent is forced through the membrane and/or through the release orifice by hydrostatic pressure. Thus, this active agent is delivered at a controlled rate either relatively immediately, or if an enteric coating is present, shortly after the device passes into the small intestine. As the active agent layer is depleted and water continues to be imbibed, the delay jacket is selectively dissolved. As the delay jacket is exhausted of soluble components, the water reaches the core, dissolving or suspending the active agent therein. This active agent is then forced through the membrane and/or through the release orifice by hydrostatic pressure and delivered at a controlled rate. In this manner, the active agent is delivered in an intermittent fashion. To deliver more than two doses of active agent, the device may be further modified by adding additional alternate layers of the delay jacket and the active agent layer over the first active agent layer.

The following examples are presented to further illustrate and explain the present invention and should not be taken as limiting in any regard.

EXAMPLES

Example 1

Preparation of colonic delivery device

A colonic delivery device is prepared from the following ingredients:

| INGREDIENTS | QUANTITY (mg) |
| --- | --- |
| Core | |
| Metoprolol Fumarate | 190 |
| Povidone, USP | 22.2 |
| Magnesium Stearate, NF | 5.8 |
| Delay jacket | |
| Dextrates, NF | 148 |
| Microcrystalline Cellulose, NF (PH101) | 148 |
| Hydroxyethyl Cellulose, NF (250H) | 72.15 |
| Magnesium Stearate, NF | 1.85 |
| Semi-permeable membrane | |
| Cellulose acetate, NF (398-10) | 3.39 |

-continued

| INGREDIENTS | QUANTITY (mg) |
|---|---|
| Cellulose acetate, NF (320 S) | 23.49 |
| Hydroxypropyl Methylcellulose, USP (15 cps) | 1.56 |
| Polyethylene Glycol, NF (3350) | 1.56 |
| Enteric coating | |
| Methacrylic Acid Copolymer, Type C, NF | 24.72 |
| Sodium Hydroxide, NF | 0.36 |
| Polyethylene Glycol 8000, NF | 2.46 |
| Talc, USP | 2.46 |

Metoprolol fumarate and povidone are mixed together and granulated with an aqueous alcohol solution. The granulation is then dried, sized, and blended with magnesium stearate. The dried lubricated powder is compressed into tablet cores using conventional tabletting techniques.

Add the dextrates, microcrystalline cellulose, and hydroxyethyl cellulose to a planetary mixer. Pass the magnesium stearate through a screen and add to mixer. Blend for approximately five minutes.

Add approximately 185 mg of the above mixture to the die cavity of a Colson single-punch tablet press fitted with a 14/32" tablet punch. Place one of the active cores onto the lower layer and add another 185 mg of the mixture. Compress the materials to form a press-coated, jacketed tablet.

Combine 456 mg methylene chloride and 114 mg methyl alcohol on a per tablet basis to form a solution. Dissolve the semi-permeable membrane ingredients in the solution using a propeller type mixer.

Spray coat the jacketed tablets with the above solution in a UniGlatt Coater using the following parameters:

| Inlet Air Temperature | 45–50° C. |
|---|---|
| Atomizing Air Pressure | 2.0 Bar |
| Spray Rate | 15–25 ml/min |

Drill the coated tablets with a 0.040" mechanical drill bit using a hand drill and laboratory arrangement.

For 100 grams of enteric coating dispersion, add 20 g of methacrylic acid copolymer to 45.4 g of water while mixing. In a second container, mix 0.3 g of sodium hydroxide with 6.7 g of water and add this mixture to the first container. In a third container, mix 2.0 g of polyethylene glycol with 15.1 g of water and add this to the first container. Continue to mix while adding 2.0 g of talc and 8.5 g of water to form a suspension.

Apply the above suspension to the coated tablets in a Glatt GC 300 12" Perforated Pan Coater using the following parameters:

| Inlet Air Temperature | 50–65° C. |
|---|---|
| Atomizing Air Pressure | 2.5 Bar |
| Nozzle Size and Type | 1.1 mm, 35° |
| Spray Rate | 15–22 ml/min |

Example 2

Dissolution test

The release rate of a tablet of Example 1 was determined using a two-hour presoak in 0.1N HCl and then a standard dissolution test using USP Rotating Basket and the following parameters:

| Stir Rate | 100 rpm |
|---|---|
| Wavelength | 275 nm |
| Temperature | 37° C. |
| Medium | 0.1 N HCL @ 0–2 hr, phosphate buffer (pH = 7.5) @ 2–24 hr |

The results of the dissolution test were as follows:

| Timepoint (hours) | Total Release (% Total) | Rate (%/hr) |
|---|---|---|
| 0–2 | <0.5 | negligible |
| 3–5 | <0.5 | negligible |
| 6 | 1.7 | 1.3 |
| 7–8 | 16.5 | 7.4 |
| 9–10 | 33.6 | 8.6 |
| 11–12 | 48.3 | 7.4 |
| 13–14 | 61.0 | 6.4 |
| 15–18 | 76.2 | 3.8 |
| 19–24 | 82.7 | 1.1 |

Example 3

Aqueously administrable semi-permeable membrane

A controlled release delivery device in which the semi-permeable membrane is applied aqueously is prepared from the following ingredients:

| INGREDIENTS | QUANTITY |
|---|---|
| Core | per tablet (mg) |
| Acetaminophen | 80.0 |
| Maltitol | 98.0 |
| Hydroxypropyl Methylcellulose, 15 cps | 10.0 |
| Polyethylene Glycol, 8000 | 10.0 |
| Magnesium Stearate | 2.0 |
| Delay Jacket | per tablet (mg) |
| Dextrates | 409.0 |
| Polyethylene Glycol, 8000 | 23.2 |
| Hydroxypropyl Methylcellulose, 15 cps | 23.2 |
| Magnesium Stearate | 4.6 |
| Semi-permeable membrane | per 1000 g dispersion (g) |
| Cellulose Acetate Latex, 25% (prepared from cellulose acetate, USP) | 121.2 |
| Glyceryl Triacetate | 45.5 |
| Hydroxypropyl Methylcellulose, 15 cps | 3.3 |
| Talc | 3.3 |
| Deionized Water | 826.7 |

All core components are mixed together and sized. The mixture is then pressed into tablet cores using conventional tabletting techniques.

All delay jacket components are next sized and blended. The jacket is compressed around the drug core by partially filing a larger die cavity of a tablet punch with the jacket blend, placing a tablet core onto this layer and adding further jacket blend to fill the die cavity. The materials are then compressed to form a press-coated, jacketed tablet.

Stir together glyceryl triacetate, hydroxypropyl methylcellulose and talc to form a slurry. Add all of the deionized water while continuing to stir. When a uniform mixture of all components has formed, add the cellulose acetate latex and continue to mix the dispersion. Spray coat the jacket tablets to the desired membrane weight with this dispersion using a perforated pan coater with the following set points:

| | |
|---|---|
| Nozzle Size | 1.0 mm Inlet Air |
| Temperature | 68° C. |
| Flowrate | 135 m³/h |
| Pump Rate | 10 ml/min |
| Drum Speed | 6.5 rpm |
| Atomizing Air Pressure | 2.0 bar |

Drill the coated tablets with a 0.25 mm drill-bit to a depth of approximately 1 mm.

The above coated tablets can be coated with an enteric dispersion as in example 1.

Example 4

Preparation of an Intermittent Device

| Ingredient | Quantity |
|---|---|
| Placebo Core | per tablet (mg) |
| dextrates | 178.0 |
| hydroxypropyl methylcellulose, 15 cps | 10.0 |
| polyethylene glycol 8000 | 10.0 |
| magnesium stearate | 2.0 |
| Drug Sub-coat | per 1000 g of solution (g) |
| phenylpropanolamine HCl | 126.0 |
| hydroxypropyl methylcellulose, 15 cps | 25.0 |
| polyethylene glycol 8000 | 10.0 |
| deionized water | 839.0 |
| Delay Jacket | per tablet (mg) |
| dextrates | 409.0 |
| hydroxypropyl methylcellulose, 15 cps | 23.2 |
| polyethylene glycol 8000 | 23.2 |
| magnesium stearate | 4.6 |
| Semipermeable Membrane | per 1000 g of dispersion (g) |
| cellulose acetate 398-10 (25% aqueous dispersion) | 121.2 |
| glyceryl triaceate | 45.5 |
| hydroxypropyl methylcellulose, 15 cps | 3.3 |
| talc | 3.3 |
| deionized water | 826.7 |
| Drug Over-coat | per 1000 g of solution (g) |
| phenylpropanolamine HCl | 98.0 |
| hydroxypropyl methylcellulose, 15 cps | 11.0 |
| polyethylene glycol 8000 | 22.0 |
| deionized water | 869.0 |

All core components are mixed together and sized. The mixture is then pressed into tablet cores using conventional tabletting techniques.

To prepare the sub-coat, heat approximately one-third of the water to near boiling and add the hydroxypropyl methylcellulose followed by the polyethylene glycol with stirring. Remove from heat and add the Phenylpropanolamine HCl followed by the remaining water. Continue to stir until a clear solution is formed. Spray the drug solution onto the placebo cores in a perforated pan coater using the following set-points:

| | |
|---|---|
| Inlet air temperature | 68° C. |
| Air volume flowrate | 135 m³/h |
| Pump rate | 18.9% |
| Drum speed | 13.5 rpm |
| Atomizing air pressure | 2.00 bar |
| Nozzle size | 0.8 mm |

Stop the process when approximately 32.1 mg of drug sub-coat (corresponding to 22.5 mg of Phenylpropanolamine HCl) has been applied to the tablets on an individual tablet basis.

The delay jacket and semipermeable membrane are applied as in example 5. The drug over-coat is applied in a manner similar to the drug sub-coat. The coating process is stopped when approximately 30 mg of over-coat is applied (corresponding to 22.5 mg of Phenylpropanolamine HCl).

Drill the tablets using a 0.25 mm drill bit and a mechanical arrangement to provide a release orifice.

The above description is for the purpose of teaching the person of ordinary skill in the art how to practice the present invention and it is not intended to detail all those obvious modifications and variations of it which will become apparent to the skilled worker upon reading the description. It is intended, however, that all such obvious modifications and variations be included within the scope of the present invention and by the following claims.

What is claimed is:

1. A drug delivery device which comprises:
   a) a solid core comprising a pharmaceutical or veterinary active agent;
   b) a substantially soluble delay jacket coated over the core through which the active agent can diffuse, the delay jacket comprising at least one component selected from the group consisting of a binder, an osmotic agent, and a lubricant;
   c) a semi-permeable membrane coated over the delay jacket and
   d) an additional layer of active agent.

2. The device of claim 1, further comprising an enteric coating over the semi-permeable membrane.

3. The device of claim 1, wherein the semi-permeable membrane has a release orifice.

4. The device of claim 1, wherein the active agent is selected from the group consisting of proteins, peptides, antiasthmatics, antianginals, corticosteroids, 5-lipoxygenase inhibitors, antihypertensives, and leukotriene $B_4$ receptor antagonists.

5. The device of claim 1, wherein the active agent is selected from the group consisting of theophylline, IGF-I, PTH (1–34), $TGF_\alpha$,$TGF_{\beta 1}$, $TGF_{\beta 2}$,$TGF\beta_3$,$IFN_\alpha$, hybrid $IFN_\alpha$, $IFN_\gamma$, hirudin, heparin, calcitonin, 5-aminosalicylic acid, N-hydroxy-N-((6-phenoxy-2H-1-benzopyran-3-yl)methyl)-urea, 4-[5-[4-(aminoiminomethyl)phenoxy]pentoxy]-3-methoxy-N,N-bis(1-methylethyl)benzamide (Z)-2-butenedioate, N-[2-[[2-[[4-(4-fluorophenyl)phenyl]methyl]-1,2,3,4-tetrahydro-1-oxo-6-isoquinolinyl]oxy]ethyl]-N-hydroxyurea, 1-(1-benzo[b]thien-2-ylethyl)-1-hydroxyurea, 5-[2-(2-carboxyethyl)-3-{6-(para-methoxyphenyl)-5E-hexenyl}oxyphenoxy] valeric acid, beclomethasone dipropionate, betamethasone-17-valerate, prednisolone metasulfobenzoate, tixocortol pivalate, budesonide, fluticasone, and metoprolol, or pharmaceutically acceptable salts thereof.

6. The device of claim 1, wherein the delay jacket limits the release of the active agent from the drug core to no more than 10% for three hours in intestinal fluid.

7. The device of claim 1, wherein the delay jacket comprises an osmotic agent.

8. The device of claim 7, wherein the delay jacket further comprises at least one excipient selected from the group consisting of a binder, a hygroscopic suspending or thickening agent, and a tablet lubricant.

9. The device of claim 1, wherein the semi-permeable membrane comprises a compound selected from the group consisting essentially of cellulose acetate, ethylcellulose, polymethacrylic acid esters and acrylic acid ester/ methacrylic acid copolymer, the copolymer having quarternary ammonium groups.

10. The device of claim 1, wherein the semi-permeable membrane comprises at least one aqueously dispersible pharmaceutically acceptable polymeric compound.

11. The device of claim 10, wherein the compound is selected from the group consisting of methacrylic ester copolymers, poly(ethyl acrylate, methyl methacrylate), poly(ethyl acrylate, methyl methacrylate, trimethylammonioethyl methacrylate chloride), polymethyl methacrylate-methacrylic acid copolymers, cellulose acetate, ethylcellulose, cellulose acetate phthalate, and hydroxypropyl methylcellulose phthalate.

12. The device of claim 2, wherein the enteric coating is selected from the group consisting of cellulose acetate phthalate NF, hydroxypropyl methylcellulose phthalate NF, polyvinyl acetate phthalate NF, and methacrylic acid copolymer NF.

13. The device of claim 2, wherein the additional layer of active agent is between the semi-permeable membrane and the enteric coating.

14. The device of claim 2, wherein the additional layer of active agent is over the enteric coating.

15. The device of claim 3, wherein the release orifice is between about 0.05 mm and 1.5 mm.

16. The device of claim 2, wherein at least 50% of the active agent is delivered to the colon.

17. The device of claim 1, wherein the additional layer of active agent is between the delay jacket and the semi-permeable membrane.

18. A method of delivering an active agent to the lower portion of the small intestine of an animal in need thereof, said method consisting of orally administering the device of claim 2 to said animal.

19. A method of delivering a colonically active or colonically absorbable active agent to the colon of an animal in need thereof, said method consisting of orally administering the device of claim 2 to said animal.

20. The method of claim 19, wherein the active agent is delivered at a rate of from about 5% to about 25% by weight per hour in the colon.

21. A method of making an orally administrable active agent delivery device which comprises:
   a) forming a solid core comprising a pharmaceutical or veterinary active agent;
   b) coating said core with a substantially soluble delay jacket through which the active agent can diffuse, the delay jacket comprising at least one component selected from the group consisting of a binder, an osmotic agent, and a lubricant;
   c) coating said delay jacket with a semi-permeable membrane; and
   d) adding an additional layer of active agent, said additional layer of active agent being:
      i) between the delay jacket and the semi-permeable membrane; or
      ii) outside of the semi-permeable membrane.

22. The method according to claim 21, wherein the semi-permeable membrane is applied as aqueous dispersion.

23. A method of making an orally administrable active agent delivery device which comprises:
   a) forming a solid core comprising a pharmaceutical or veterinary active agent;
   b) coating said core with a substantially soluble delay jacket through which the active agent can diffuse, the delay jacket comprising at least one component selected from the group consisting of a binder, an osmotic agent, and a lubricant;
   c) coating said delay jacket with a semi-permeable membrane;
   d) coating said semi-permeable membrane with an enteric coating; and
   e) adding an additional layer of active agent, said additional layer of active agent being:
      i) between the delay jacket and semi-permeable membrane;
      ii) between the semi-permeable membrane and the enteric coating; or
      iii) outside of the enteric coating.

* * * * *